United States Patent
Ure et al.

(10) Patent No.: US 9,975,839 B2
(45) Date of Patent: May 22, 2018

(54) PARAXYLENE EXTRACTION OF PURIFICATION MOTHER LIQUOR WITH HEAT INTEGRATION

(71) Applicant: INVISTA TECHNOLOGIES S.À R.L., Gallen (CH)

(72) Inventors: Alan Macpherson Ure, Redcar (GB); Antony Peter John Limbach, Redcar (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days. days.

(21) Appl. No.: 15/513,373

(22) PCT Filed: Sep. 23, 2015

(86) PCT No.: PCT/EP2015/071910
§ 371 (c)(1),
(2) Date: Mar. 22, 2017

(87) PCT Pub. No.: WO2016/046284
PCT Pub. Date: Mar. 31, 2016

(65) Prior Publication Data
US 2017/0240497 A1    Aug. 24, 2017

(30) Foreign Application Priority Data
Sep. 24, 2014 (GB) .................................. 1416838.9

(51) Int. Cl.
| | | |
|---|---|---|
| C07C 51/42 | (2006.01) | |
| C07C 51/16 | (2006.01) | |
| B01D 11/04 | (2006.01) | |
| B01D 3/14 | (2006.01) | |
| B01D 17/02 | (2006.01) | |

(52) U.S. Cl.
CPC .............. *C07C 51/16* (2013.01); *B01D 3/143* (2013.01); *B01D 11/043* (2013.01); *B01D 11/0492* (2013.01); *B01D 17/02* (2013.01)

(58) Field of Classification Search
CPC .............. B01D 11/043; B01D 11/0492; B01D 11/0426; B01D 17/02; B01D 3/143; C07C 51/16; C07C 51/44; C07C 51/48; C07C 63/26; C07C 51/265
See application file for complete search history.

(56) References Cited

U.S. PATENT DOCUMENTS
2,833,816 A    5/1958 Saffer et al.

FOREIGN PATENT DOCUMENTS
| CN | 101914013 A | 12/2010 |
|---|---|---|
| EP | 0962442 | * 6/1999 |
| EP | 0962442 A1 | 12/1999 |
| WO | 2011/146242 A2 | 11/2011 |
| WO | 2016/046284 A1 | 3/2016 |

OTHER PUBLICATIONS

Li et al., "Water-Saving Method for Producing Terephthalic Acid", Database CA [online] Chemical Abstracts Service, Columbus, Ohio, US, XP002750932, retrieved from STN Database accession No. 2010:1576461. (Mechanical Translation).
International Search Report and Written Opinion Received for PCT Application No. PCT/EP2015/071910, dated Apr. 12, 2015, 9 pages.
International Preliminary Report on Patentability Report Received for PCT Patent Application No. PCT/EP2015/071910, dated Mar. 28, 2017, 6 pages.

* cited by examiner

*Primary Examiner* — Yevgeny Valenrod
*Assistant Examiner* — Blaine G Doletski
(74) *Attorney, Agent, or Firm* — William J. Simmons

(57) ABSTRACT

The present invention provides a process for the production of an aromatic dicarboxylic acid comprising the catalytic oxidation of a hydrocarbon precursor in an organic solvent, comprising the steps of: i) separating a vent gas from an oxidation stage into an organic solvent-rich liquid stream and a water-rich vapor stream in a distillation stage; and ii) separating an aqueous purification mother liquor comprising organic compounds from purified aromatic dicarboxylic acid crystals in a separation stage, characterized in that the process further comprises the steps of: iii) transferring the aqueous purification mother liquor from the separation stage to an extraction stage; iv) extracting said organic compounds from the aqueous purification mother liquor by contacting the aqueous purification mother liquor at a temperature of at least 90° C. with an organic liquid in the extraction stage to form an aqueous phase and an organic phase, wherein the concentration of said organic compounds in the aqueous phase is lower than the concentration of said organic compounds in the aqueous purification mother liquor; and v) transferring the aqueous phase to said distillation stage. The present invention further provides an apparatus for carrying out the process.

36 Claims, 1 Drawing Sheet

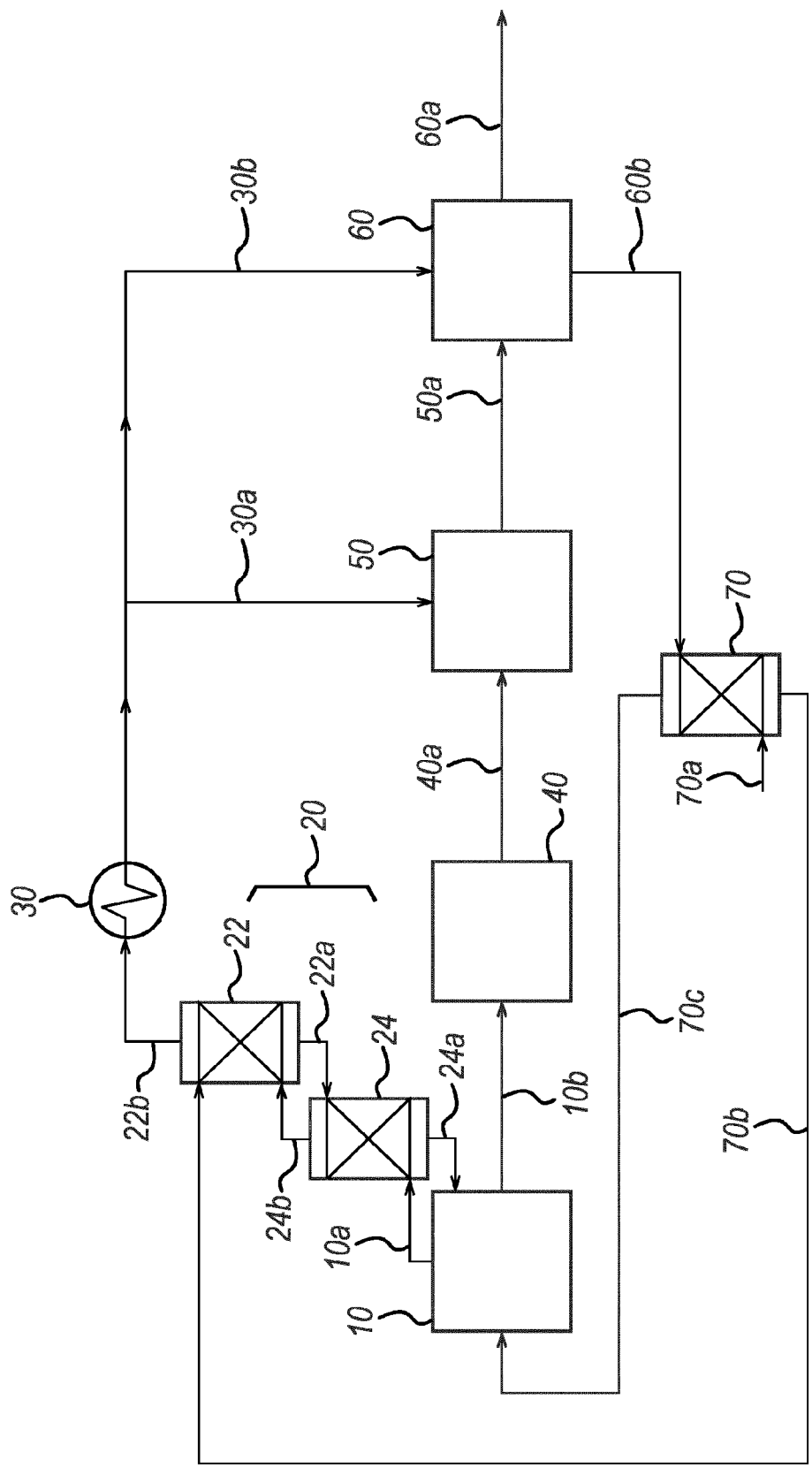

PARAXYLENE EXTRACTION OF PURIFICATION MOTHER LIQUOR WITH HEAT INTEGRATION

TECHNICAL FIELD

The present invention relates to a process and apparatus for the production of an aromatic dicarboxylic acid.

BACKGROUND ART

Aromatic dicarboxylic acids are commonly manufactured by the catalytic oxidation of a hydrocarbon precursor in an organic solvent. An example is terephthalic acid (TA), which is widely used in the manufacture of polyesters, such as poly(ethylene terephthalate) (PET). The TA required as a reactant for PET production is known as "purified terephthalic acid" (PTA) and generally contains over 99.97 wt %, preferably over 99.99 wt %, of terephthalic acid, and less than 25 ppm 4-carboxybenzaldehyde (4-CBA). On the commercial scale, PTA suitable for use in PET production is generally prepared in a two-stage process. First, p-xylene is oxidized (e.g. in air) in the presence of a metal catalyst (e.g. a cobalt and/or manganese salt or compound) to provide "crude terephthalic acid" (CTA), as described in, for example, U.S. Pat. No. 2,833,816. Second, the CTA produced by this oxidation reaction is then purified, as it is typically contaminated by impurities such as 4-CBA, p-toluic acid, and various coloured impurities that impart a yellowish colour to the TA. Purification of the CTA typically requires at least one chemical transformation (e.g. hydrogenation) in addition to at least one physical procedure (e.g. crystallization, washing, etc.) to yield PTA.

PTA is generally considered to be a commodity item, with several million tonnes being produced annually, and it is therefore desirable for manufacturers to reduce their costs to maximise the economy and efficiency of PTA production. This can be achieved both by reducing capital costs (e.g. equipment costs) and variable costs (e.g. costs associated with waste disposal, use of starting materials, organic solvent, heating fuel and demineralised water).

EP-A-0962442 discloses a process in which an aqueous purification mother liquor from which PTA crystals have been separated is guided to a cooling vessel and cooled to precipitate organic compounds, such as p-toluic acid. These organic compounds are separated in a separator from the mother liquor, which is then subjected to a p-xylene extraction and used as slurrying water and as reflux to a middle portion of a distillation column for separating acetic acid and water. However, this cooling and filtering process not only results in the loss of heat from the aqueous purification mother liquor and thus from the distillation column, it also results in the removal of valuable organic compounds, including compounds that may be oxidised to TA as well as minor amounts of TA itself, from the reaction system.

It is an object of the present invention to provide a more economic and efficient process and apparatus for the manufacture of aromatic dicarboxylic acids and, in particular, to provide a process and apparatus that overcome the aforementioned disadvantages. Further objects will be apparent from the description below.

DISCLOSURE OF THE INVENTION

The present invention provides a process for the production of an aromatic dicarboxylic acid comprising the catalytic oxidation of a hydrocarbon precursor in an organic solvent, comprising the steps of:

i) separating a vent gas from an oxidation stage into an organic solvent-rich liquid stream and a water-rich vapour stream in a distillation stage; and ii) separating an aqueous purification mother liquor comprising organic compounds from purified aromatic dicarboxylic acid crystals in a separation stage, characterised in that the process further comprises the steps of:

iii) transferring the aqueous purification mother liquor from the separation stage to an extraction stage;

iv) extracting said organic compounds from the aqueous purification mother liquor by contacting the aqueous purification mother liquor at a temperature of at least 90° C. with an organic liquid in the extraction stage to form an aqueous phase and an organic phase, wherein the concentration of said organic compounds in the aqueous phase is lower than the concentration of said organic compounds in the aqueous purification mother liquor; and v) transferring the aqueous phase to said distillation stage.

Step iii) may comprise diluting the aqueous purification mother liquor with an aqueous liquid (e.g. water). Step iii) may comprise heating the aqueous purification mother liquor. These steps may be included to dissolve any solid organic compounds present in the aqueous purification mother liquor, which could not only cause clogging of the extraction stage but could also cause loss of control of the interface between the aqueous phase and the organic phase in the extraction stage, leading to carry-over of organic liquid in the aqueous phase or vice versa. A further option for avoiding the presence of small amounts of solid organic compounds in the aqueous purification mother liquor fed to the extraction stage is for step iii) to comprise filtering the aqueous purification mother liquor. However, this option is less preferred because it results in removal of the organic compounds from the aqueous purification mother liquor, preventing the recovery of these organic compounds into the organic phase. Accordingly, the aqueous purification mother liquor may be transferred in step iii) from the separation stage to the extraction stage without being subject to an intermediate cooling step followed by an intermediate separation step, thus avoiding the removal of organic compounds from the aqueous purification mother liquor by this mechanism.

The present invention further provides an apparatus for the production of an aromatic dicarboxylic acid comprising:

a) a distillation stage configured to separate a vent gas from an oxidation stage into an organic solvent-rich liquid stream and a water-rich vapour stream; and b) a separation stage configured to separate an aqueous purification mother liquor comprising organic compounds from purified aromatic dicarboxylic acid crystals;

characterised in that the apparatus further comprises:

c) an extraction stage configured to receive the aqueous purification mother liquor from the separation stage and to extract said organic compounds from the aqueous purification mother liquor by contacting the aqueous purification mother liquor at a temperature of at least 90° C. with an organic liquid to form an aqueous phase and an organic phase, wherein the concentration of said organic compounds in the aqueous phase is lower than the concentration of said organic compounds in the aqueous purification mother liquor; wherein the extraction stage is further configured to transfer the aqueous phase to said distillation stage.

The apparatus may further comprise means to dilute the aqueous purification mother liquor with an aqueous liquid before it is received by the extraction stage. The apparatus may further comprise means to heat the aqueous purification mother liquor before it is received by the extraction stage. These features may be included to dissolve any solid organic compounds present in the aqueous purification mother liquor, which could not only cause clogging of the extraction stage but could also cause loss of control of the interface between the aqueous phase and the organic phase in the extraction stage, leading to carry-over of organic liquid in the aqueous phase or vice versa. A further option for avoiding the presence of small amounts of solid organic compounds in the aqueous purification mother liquor fed to the extraction stage is for the apparatus to further comprise means to filter the aqueous purification mother liquor. However, this option is less preferred because it results in removal of the organic compounds from the aqueous purification mother liquor, preventing the recovery of these organic compounds into the organic phase. Accordingly, the extraction stage may be configured to receive the aqueous purification mother liquor from the separation stage without an intermediate cooling step followed by an intermediate separation step, thus avoiding the removal of organic compounds from the aqueous purification mother liquor by this mechanism.

The present inventors have found that an aqueous phase suitable for return to the distillation stage can be extracted from aqueous purification mother liquor at a temperature of at least 90° C. The present process and apparatus allow the reuse of the aqueous phase, thus reducing water usage and eliminating a potential effluent stream, whilst avoiding the capital and variable costs of carrying out intermediate cooling and separation steps on the aqueous purification mother liquor.

BRIEF DESCRIPTION OF THE DRAWINGS

FIG. 1 is a schematic of a process and apparatus according to the invention.

DETAILED DESCRIPTION OF THE INVENTION

Various embodiments of the invention are described herein. It will be recognised that features specified in each embodiment may be combined with other specified features to provide further embodiments.

It will be appreciated that the general operation of a process and apparatus for the production of an aromatic dicarboxylic acid by the catalytic oxidation of a hydrocarbon precursor in an organic solvent is well known. For example, as discussed above, terephthalic acid suitable for use in PET production (i.e. purified terephthalic acid) is generally prepared in a two-stage process. First, p-xylene is oxidized (e.g. in air) in the presence of a metal catalyst (e.g. a cobalt and/or manganese salt or compound) to provide crude terephthalic acid (step i) and stage a) above form part of this stage). Second, the crude terephthalic acid produced by this oxidation reaction is then purified to remove impurities, such as 4-CBA and p-toluic acid, to yield purified terephthalic acid (step ii) and stage b) above form part of this stage). Purification of crude terephthalic acid typically requires at least one chemical transformation (e.g. hydrogenation) in addition to at least one physical procedure (e.g. crystallization, washing, etc.).

Aromatic Dicarboxylic Acid

The aromatic dicarboxylic acid produced in the process and apparatus of the present invention is preferably selected from terephthalic acid, orthophthalic acid and isophthalic acid. The aromatic dicarboxylic acid is preferably terephthalic acid. The hydrocarbon precursor is a compound that may be oxidised to form the aromatic dicarboxylic acid. Thus, the hydrocarbon precursor is typically benzene or naphthalene substituted with groups such as $C_{1-6}$alkyl, formyl, or acetyl in the positions of the carboxylic acid substituents in the desired end product. Preferred hydrocarbon precursors are $C_{1-6}$alkyl-substituted benzene, in particular p-xylene. The organic solvent is typically an aliphatic carboxylic acid, such as acetic acid, or a mixture of such aliphatic carboxylic acid(s) and water. The oxidation reaction may be carried out under any conditions wherein oxygen is available, e.g. the reaction can be carried out in air. The reaction catalyst typically comprises soluble forms of cobalt and/or manganese (e.g. their acetates), with a source of bromine, such as hydrogen bromide, used as a promoter. The temperature of the oxidation reaction is typically in the range of about 100-250° C., preferably about 150-220° C. Any conventional pressure may be used for the reaction, suitably to maintain the reaction mixture in a liquid state.

The organic compounds that are extracted from the aqueous purification mother liquor typically comprise terephthalic acid itself, p-toluic acid, benzoic acid or a mixture thereof. A portion or the entirety of each organic compound may be extracted from the aqueous purification mother liquor. Preferably, the organic compounds comprise p-toluic acid, benzoic acid or a mixture thereof.

Oxidation Stage

The oxidation stage typically comprises an oxidation reactor and performs the function of catalytically oxidizing the hydrocarbon precursor in the organic solvent, thus forming a product stream and the vent gas. The product stream is typically transferred to a crystallisation stage to form a first slurry of crude aromatic dicarboxylic acid crystals and an overhead vapour. The first slurry of crude aromatic dicarboxylic acid crystals is typically passed to a separation stage in which a mother liquor is separated from the crude aromatic dicarboxylic acid crystals, which may then be mixed with an aqueous liquid to form a second slurry of crude aromatic dicarboxylic acid crystals. This second slurry of crude aromatic dicarboxylic acid crystals is typically transferred to a purification plant, heated and subjected to hydrogenation, before being cooled to form a slurry of purified aromatic dicarboxylic acid crystals.

The vent gas from the oxidation stage is separated in the distillation stage into an organic solvent-rich liquid stream and a water-rich vapour stream. The organic solvent-rich liquid stream from the distillation stage typically comprises 80-95% w/w of the organic solvent and is typically returned to the oxidation stage. The water-rich vapour stream from the distillation stage typically comprises 0.1-5.0% w/w of the organic solvent and is typically condensed to form a condensate stream and an overhead gas in a condensing stage. A portion of the condensate stream is typically used as a source of the aqueous liquid used to form the second slurry of crude aromatic dicarboxylic acid crystals mentioned above. A portion of the condensate stream also typically forms a source of wash fluid for the purified aromatic dicarboxylic acid crystals from the purification plant.

Distillation Stage

The distillation stage typically comprises a first distillation column. The distillation stage may further comprise a second distillation column. Preferably, the first and second distillation columns are connected in series. The distillation stage may comprise further distillation columns. Again, the further distillation columns are preferably connected in series to the first and second distillation columns.

If the distillation stage is made up of one distillation column, the first distillation column may be configured to receive the vent gas from the oxidation stage and pass an organic solvent-rich liquid stream to the oxidation stage and a water-rich vapour stream to the condensing stage. If the distillation stage is made up of two distillation columns, the second distillation column is preferably configured to receive the vent gas from the oxidation stage and pass an organic solvent-rich liquid stream to the oxidation stage and a water-rich vapour stream to the first distillation column, which is preferably configured to pass a water-rich liquid stream to the second distillation column and a water-rich vapour stream to the condensing stage (i.e. the water-rich vapour stream travels from the second distillation column to the first distillation column and then from the first distillation column to the condensing stage). If the distillation stage comprises any further distillation column(s), the further distillation column(s) are preferably configured to receive the vent gas from the oxidation stage and pass an organic solvent-rich liquid stream to the oxidation stage and a vapour stream to the second distillation column, which is preferably configured to pass a liquid stream to the further distillation column(s) and a water-rich vapour stream to the first distillation column, which is preferably configured to pass a water-rich liquid stream to the second distillation column and a water-rich vapour stream to the condensing stage (i.e. the water-rich vapour stream travels from the further distillation column(s) to the second distillation column, and then from the second distillation column to the first distillation column, and then from the first distillation column to the condensing stage).

The distillation column(s) are typically pressurised distillation columns, which are also known as rectifiers. The distillation column(s) typically comprise a plurality of stages known in the art as theoretical stages, which can be provided by trays, such as sieve, valve or bubble cap trays, structured packing or other suitable structures that provide surfaces for mass transfer between gaseous and liquid phases within the column(s).

The aqueous phase from the extraction stage may be transferred to an upper region of the first distillation column. Therefore, if the first distillation column comprises a plurality of theoretical stages, the aqueous phase may be transferred to the top theoretical stage of the first distillation column. Accordingly, if the first distillation column comprises at least 10 theoretical stages, at least 20 theoretical stages, at least 30 theoretical stages, or at least 40 theoretical stages, the aqueous phase may be transferred to one of the top 8 theoretical stages, or one of the top 5 theoretical stages, or one of the top 2 theoretical stages of the first distillation column. Preferably, the aqueous phase is transferred to the top theoretical stage of the first distillation column. Similarly, if the first distillation column comprises a plurality of trays, the aqueous phase may be transferred to the top tray of the first distillation column. Accordingly, if the first distillation column comprises at least 20, at least 30, at least 40, at least 50 trays, at least 60 trays, or at least 70 trays, the aqueous phase may be transferred to one of the top 10 trays, or one of the top 5 trays, or one of the top 2 trays of the first distillation column. Preferably, the aqueous phase is transferred to the top tray of the first distillation column. The extraction carried out on the aqueous purification mother liquor reduces or eliminates the presence of solid organic compounds in the aqueous phase, thus allowing its transfer to the top stage and/or tray of the first distillation column. Accordingly, it is not necessary to include extra stages and/or trays in the first distillation column to remove these solids to avoid contaminating the water-rich vapour stream. Therefore, the capital cost associated with such extra stages and/or trays is avoided.

Separation Stage

The separation stage may comprise a separator, such as a centrifuge or a filter. A preferred filter is a rotary filter, which provides the advantage of allowing a number of process steps to be carried out within a single piece of equipment. Specifically, a rotary filter may be used to separate a slurry of purified aromatic dicarboxylic acid crystals from the aqueous purification mother liquor before subjecting the purified aromatic dicarboxylic acid crystals to subsequent treatments (e.g. washing and drying) and then discharging them.

Typically, a filter is used in the separation stage and the purified aromatic dicarboxylic acid crystals are washed on the filter with a wash fluid that may be derived from a condensate stream from the condensing stage (i.e. the wash fluid is ultimately derived from the water-rich vapour stream from the distillation stage). The wash fluid may then be combined with the aqueous purification mother liquor that is transferred to the extraction stage. As mentioned above, the aqueous purification mother liquor may be diluted with other aqueous liquid streams (e.g. water streams) prior to entering the extraction stage, for instance by combining the aqueous purification mother liquor with these streams in a collection drum.

The purity of the purified aromatic dicarboxylic acid crystals obtained from the separation stage is affected by the level of organic compounds in the condensate stream from the condensing stage (since this condensate stream is typically used as a source for the aqueous liquid used to form the second slurry of crude aromatic dicarboxylic acid crystals mentioned above and/or as a source for the wash fluid for the purified aromatic dicarboxylic acid crystals) as well as by the purity of the first slurry of crude aromatic dicarboxylic acid crystals mentioned above, which is in turn influenced by the conditions in the oxidation stage. For example, p-toluic acid is a common impurity in PTA crystals. P-toluic acid is directly produced by the oxidation of p-xylene in the oxidation stage and is also produced by the hydrogenation of a further impurity that is present in CTA, namely 4-CBA, in the purification plant. The level of 4-CBA in CTA, and thus the level of p-toluic acid in PTA, can be reduced by carrying out the oxidation reaction under more aggressive conditions (e.g. at a higher temperature). However, these conditions result in increased degradation of p-xylene starting material and acetic acid solvent, thus increasing the variable cost associated with raw materials.

The process and apparatus of the present invention carry out an extraction on the aqueous purification mother liquor that is fed to the distillation stage that reduces the levels of organic compounds (such as p-toluic acid) in the water-rich vapour stream that is passed from the distillation stage to the condensing stage, and thus reduces the levels of these organic compounds in the condensate stream from the condensing stage. A portion of the condensate stream is typically used as a source of the aqueous liquid used to form the second slurry of crude aromatic dicarboxylic acid crystals mentioned above and a portion of the condensate stream also typically forms a source of wash fluid for the purified aromatic dicarboxylic acid crystals from the purification plant. Accordingly, the purity of the purified aromatic dicarboxylic acid crystals obtained from the purification plant may be increased and/or the effectiveness of the wash fluid in removing undesired organic compounds (such as p-toluic acid) from the purified aromatic dicarboxylic acid crystals may be increased. Therefore, the process and apparatus of the present invention allow a given purity specification of the purified aromatic dicarboxylic acid crystals (e.g. PTA comprising less than 200 ppm p-toluic acid) to be achieved under milder oxidation reaction conditions, e.g. a greater 4-CBA content can be tolerated in the CTA in the process and apparatus of the present invention.

Extraction Stage

The extraction stage may comprise an extractor, such as an extraction column. Similarly to the distillation column(s), the extraction column comprises a plurality of theoretical stages, which can be provided by trays, such as sieve, valve or bubble cap trays, random or structured packing or other suitable structures that provide surfaces for mass transfer between the two liquid phases within the column. Structured packing, which may take the form of thin sheets of corrugated metal arranged in a criss-crossing relationship to create flow channels such that their intersections create mixing points for the two liquid phases, is preferred.

The aqueous purification mother liquor is typically fed to an upper region of the extraction column, whilst the organic liquid employed in the extraction stage is typically fed to a lower region of the extraction column. The aqueous phase is typically recovered from a lower region of the extraction column, in particular from the bottom of the column. The organic phase is typically recovered from an upper region of the extraction column, in particular from the top of the column.

The organic liquid may be heated prior to its contact with the aqueous purification mother liquor. This reduces or eliminates precipitation of organic compounds from the aqueous purification mother liquor and increases the difference in density between the organic phase and the aqueous phase thereby reducing the cross-sectional area required for the extraction column duty. Heating of the organic liquid is typically accomplished by transferring heat from other process streams (e.g. water streams) to the organic liquid in one or more heat exchangers. The organic liquid may be heated to a temperature approximately the same as, or close to, that of the aqueous purification mother liquor. Accordingly, the organic liquid may be heated to a temperature of at least 90° C., at least 100° C., at least 110° C., at least 120° C., at least 130° C., at least 140° C., or at least 150° C. and, typically, less than 200° C., prior to its contact with the aqueous purification mother liquor. The organic liquid preferably comprises the hydrocarbon precursor. For instance, if the aromatic dicarboxylic acid is terephthalic acid, the organic liquid may comprise p-xylene. Preferably, the organic phase is transferred from the extraction stage to the oxidation stage, suitably without passing through any of the other stages, such as the distillation stage, discussed herein, e.g. the organic phase is not transferred to the oxidation stage via the distillation stage. Accordingly, the organic phase may be transferred directly from the extraction stage to the oxidation stage. In this way, valuable organic compounds, including compounds that may be oxidised to the aromatic dicarboxylic acid as well as minor amounts of the aromatic dicarboxylic acid itself, are not lost from the reaction system but are recycled to the oxidation stage, reducing the variable cost.

The aqueous purification mother liquor is at a temperature of at least 90° C. when it is contacted with the organic liquid in the extraction stage. The aqueous purification mother liquor may be at a temperature of at least 100° C., at least 110° C., at least 120° C., at least 130° C., at least 140° C., or at least 150° C. and, typically, less than 200° C., when it is contacted with the organic liquid in the extraction stage. Typically, the aqueous purification mother liquor is at a temperature of about 150° C. when it is contacted with the organic liquid in the extraction stage. As mentioned above, the aqueous purification mother liquor may be transferred from the separation stage to the extraction stage without being subject to an intermediate cooling step followed by an intermediate separation step (i.e. there is no deliberate cooling of the aqueous purification mother liquor using a piece of equipment intended for that purpose). Nevertheless, the temperature of the aqueous purification mother liquor may fall (e.g. by up to 5° C.) between the separation stage and the extraction stage by normal heat loss processes (e.g. from the connecting pipework). As mentioned above, the aqueous purification mother liquor may be heated prior to entering the extraction stage, e.g. by transferring heat to the aqueous purification mother liquor in one or more heat exchangers. As mentioned above, the aqueous purification mother liquor may be diluted with an aqueous liquid (e.g. water) prior to entering the extraction stage.

As used herein, the term "purified" aromatic dicarboxylic acid crystals refers to aromatic dicarboxylic acid crystals that have been subjected to a purification process, which, as mentioned above, typically comprises at least one chemical transformation (e.g. hydrogenation) in addition to at least one physical procedure (e.g. crystallization, washing, etc.). Accordingly, the purified aromatic dicarboxylic acid crystals (e.g. PTA crystals) preferably comprise less than 200 ppm p-toluic acid, less than 190 ppm p-toluic acid, less than 180 ppm p-toluic acid, less than 170 ppm p-toluic acid, less than 160 ppm p-toluic acid, or less than 150 ppm p-toluic acid.

The invention will be further described with reference to the FIGURE.

FIG. 1 is a schematic of a process and apparatus according to a preferred embodiment of the present invention. Oxidation reactor 10 is charged with aqueous organic solvent (preferably aqueous acetic acid), reaction catalyst and air (inlets not shown), and hydrocarbon precursor (preferably p-xylene) from organic stream 70c. Vent gas 10a is passed from oxidation reactor 10 to second distillation column 24 which, together with first distillation column 22, forms distillation stage 20. Organic solvent-rich liquid stream 24a is passed from second distillation column 24 to oxidation reactor 10. Water-rich vapour stream 24b is passed from second distillation column 24 to first distillation column 22. Water-rich liquid stream 22a is passed from first distillation column 22 to second distillation column 24. Water-rich vapour stream 22b is passed from first distillation column 22 to condensing stage 30, which comprises one or more condensers.

Product stream 10b is passed from oxidation reactor 10 to crystallisation stage 40, which comprises one or more crystallisers. Crude aromatic dicarboxylic acid slurry stream 40a is passed from crystallisation stage 40 to purification plant 50, in which crude aromatic dicarboxylic acid crystals are separated from oxidation mother liquor, reslurried with condensate stream 30a from condensing stage 30 and passed to a hydrogenation reactor and one or more crystallisers.

Purified aromatic dicarboxylic acid slurry stream 50a is passed from purification plant 50 to separator 60, in which purified aromatic dicarboxylic acid crystals are washed with condensate stream 30b from condensing stage 30. Purified aromatic dicarboxylic acid crystals stream 60a is recovered.

Aqueous purification mother liquor stream 60b is passed from separator 60 to the top of extraction column 70. Organic liquid (preferably p-xylene) stream 70a is fed to the bottom of extraction column 70. Aqueous stream 70b is recovered from the bottom of extraction column 70 and fed to the top stage of first distillation column 22. Organic stream 70c is recovered from the top of extraction column 70 and fed to oxidation reactor 10.

The invention is further illustrated by the following illustrative example, which is not intended to limit the scope of the invention described and claimed herein.

EXAMPLES

Example 1

A column having a diameter of 2" (~50 mm) and containing 4 m of stainless steel structured packing was used to simulate the extraction column used in the present invention. An aqueous feed stream representing the aqueous purification mother liquor was fed to the top of the column and a p-xylene feed stream was fed to the bottom of the column, both through appropriate distributors. Flows within the column were counter-current. The column was operated at atmospheric pressure. An aqueous product stream was withdrawn from the bottom of the column. The measured compositions, flow rates and temperatures of each stream are shown in Table 1.

TABLE 1

|  | Aqueous feed | Organic feed | Aqueous product |
|---|---|---|---|
| Acetic (% w/w) | 1.45 | 0 | — |
| Water (% w/w) | 97.93 | 0 | — |
| P-xylene (% w/w) | 0 | 100 | — |
| Methyl acetate (% w/w) | 0.27 | 0 | — |
| Benzoic acid (% w/w) | 0.0110 | 0 | 0.0053 |
| p-Toluic acid (% w/w) | 0.0473 | 0 | 0.0079 |
| Methanol (% w/w) | 0.29 | 0 | — |
| Total rate (kg/hr) | 64 | 16 | 64 |
| Temperature (° C.) | 90 | 90 | 90 |

The invention claimed is:

1. A process for the production of an aromatic dicarboxylic acid comprising the catalytic oxidation of a hydrocarbon precursor in an organic solvent, comprising the steps of:
   i) separating a vent gas from an oxidation stage into an organic solvent-rich liquid stream and a water-rich vapour stream in a distillation stage; and
   ii) separating an aqueous purification mother liquor comprising organic compounds from purified aromatic dicarboxylic acid crystals in a separation stage,
   characterised in that the process further comprises the steps of:
   iii) transferring the aqueous purification mother liquor from the separation stage to an extraction stage;
   iv) extracting said organic compounds from the aqueous purification mother liquor by contacting the aqueous purification mother liquor at a temperature of at least 90° C. with an organic liquid in the extraction stage to form an aqueous phase and an organic phase, wherein the concentration of said organic compounds in the aqueous phase is lower than the concentration of said organic compounds in the aqueous purification mother liquor; and
   v) transferring the aqueous phase to said distillation stage.

2. The process of claim 1, further comprising heating the organic liquid prior to its contact with the aqueous purification mother liquor.

3. The process of claim 1, wherein step iii) further comprises diluting the aqueous purification mother liquor with an aqueous liquid.

4. The process of claim 1, wherein step iii) further comprises heating the aqueous purification mother liquor.

5. The process of claim 1, wherein the aqueous purification mother liquor is transferred in step iii) from the separation stage to the extraction stage without being subject to an intermediate cooling step followed by an intermediate separation step.

6. The process of claim 1, wherein the distillation stage comprises a first distillation column.

7. The process of claim 6, wherein the distillation stage further comprises a second distillation column, wherein the first and second distillation columns are connected in series.

8. The process of claim 6, wherein the aqueous phase is transferred in step v) to an upper region of the first distillation column.

9. The process of claim 8, wherein the first distillation column comprises a plurality of theoretical stages and the aqueous phase is transferred in step v) to the top theoretical stage of the first distillation column.

10. The process of claim 8, wherein the first distillation column comprises a plurality of trays and the aqueous phase is transferred in step v) to the top tray of the first distillation column.

11. The process of claim 1, wherein the extraction stage comprises an extraction column.

12. The process of claim 11, wherein the extraction column contains structured packing.

13. The process of claim 1, wherein the organic liquid comprises the hydrocarbon precursor.

14. The process of claim 1, further comprising the step of:
   vi) transferring the organic phase to the oxidation stage.

15. The process of claim 1, wherein the organic liquid comprises p-xylene.

16. The process of claim 1, wherein the aromatic dicarboxylic acid is terephthalic acid.

17. The process of claim 1, wherein said organic compounds comprise p-toluic acid, terephthalic acid, benzoic acid or a mixture thereof.

18. The process of claim 17, wherein the purified aromatic dicarboxylic acid crystals comprise less than or equal to 200 ppm p-toluic acid.

19. An apparatus for the production of an aromatic dicarboxylic acid comprising:
   a) a distillation stage configured to separate a vent gas from an oxidation stage into an organic solvent-rich liquid stream and a water-rich vapour stream; and
   b) a separation stage configured to separate an aqueous purification mother liquor comprising organic compounds from purified aromatic dicarboxylic acid crystals;
   characterised in that the apparatus further comprises:
   c) an extraction stage configured to receive the aqueous purification mother liquor from the separation stage and to extract said organic compounds from the aqueous purification mother liquor by contacting the aqueous purification mother liquor at a temperature of at least 90° C. with an organic liquid to form an aqueous phase and an organic phase, wherein the concentration of said organic compounds in the aqueous phase is lower than the concentration of said organic compounds in the aqueous purification mother liquor; wherein the extraction stage is further configured to transfer the aqueous phase to said distillation stage.

20. The apparatus of claim 19, further comprising means to heat the organic liquid prior to its contact with the aqueous purification mother liquor.

21. The apparatus of claim 19, further comprising means to dilute the aqueous purification mother liquor with an aqueous liquid before it is received by the extraction stage.

22. The apparatus of claim 19, further comprising means to heat the aqueous purification mother liquor before it is received by the extraction stage.

23. The apparatus of claim 19, wherein the extraction stage is configured to receive the aqueous purification mother liquor from the separation stage without an intermediate cooling step followed by an intermediate separation step.

24. The apparatus of claim 19, wherein the distillation stage comprises a first distillation column.

25. The apparatus of claim 24, wherein the distillation stage comprises a second distillation column, wherein the first and second distillation columns are connected in series.

26. The apparatus of claim 24, wherein the extraction stage is configured to transfer the aqueous phase to an upper region of the first distillation column.

27. The apparatus of claim 26, wherein the first distillation column comprises a plurality of theoretical stages and the extraction stage is configured to transfer the aqueous phase to the top theoretical stage of the first distillation column.

28. The apparatus of claim 26, wherein the first distillation column comprises a plurality of trays and the extraction stage is configured to transfer the aqueous phase to the top tray of the first distillation column.

29. The apparatus of claim 19, wherein the extraction stage comprises an extraction column.

30. The apparatus of claim 29, wherein the extraction column contains structured packing.

31. The apparatus of claim 19, wherein the organic liquid comprises a hydrocarbon precursor for forming the aromatic dicarboxylic acid.

32. The apparatus of claim 19, wherein the extraction stage is configured to transfer the organic phase to the oxidation stage.

33. The apparatus of claim 19, wherein the organic liquid comprises p-xylene.

34. The apparatus of claim 19, wherein the aromatic dicarboxylic acid is terephthalic acid.

35. The apparatus of claim 19, wherein said organic compounds comprise p-toluic acid, terephthalic acid, benzoic acid or a mixture thereof.

36. The apparatus of claim 35, wherein the purified aromatic dicarboxylic acid crystals comprise less than or equal to 200 ppm p-toluic acid.

* * * * *